United States Patent
Frenkel et al.

(10) Patent No.: US 7,855,233 B2
(45) Date of Patent: *Dec. 21, 2010

(54) CITRATE SALT OF RASAGILINE

(75) Inventors: Anton Frenkel, Netanya (IL); Muhammad Safadi, Nazareth (IL); Tamas Koltai, Netanya (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/689,044

(22) Filed: Jan. 18, 2010

(65) Prior Publication Data

US 2010/0190859 A1 Jul. 29, 2010

Related U.S. Application Data

(63) Continuation-in-part of application No. 12/455,976, filed on Jun. 9, 2009.

(60) Provisional application No. 61/205,833, filed on Jan. 23, 2009.

(51) Int. Cl.
*A01N 33/02* (2006.01)
*A61K 31/135* (2006.01)

(52) U.S. Cl. ...................... 514/647; 514/657

(58) Field of Classification Search .................. 514/647
See application file for complete search history.

(56) References Cited

U.S. PATENT DOCUMENTS

| | | |
|---|---|---|
| 5,387,612 A | 2/1995 | Youdim et al. |
| 5,453,446 A | 9/1995 | Youdim et al. |
| 5,457,133 A | 10/1995 | Youdim et al. |
| 5,486,541 A | 1/1996 | Sterling et al. |
| 5,519,061 A | 5/1996 | Youdim et al. |
| 5,532,415 A | 7/1996 | Youdim et al. |
| 5,576,353 A | 11/1996 | Youdim et al. |
| 5,599,991 A | 2/1997 | Youdim et al. |
| 5,663,415 A | 9/1997 | Chopdekar et al. |
| 5,668,181 A | 9/1997 | Youdim et al. |
| 5,744,500 A | 4/1998 | Youdim et al. |
| 5,786,390 A | 7/1998 | Youdim et al. |
| 5,891,923 A | 4/1999 | Youdim et al. |
| 6,126,968 A | 10/2000 | Peskin et al. |
| 6,277,886 B1 | 8/2001 | Levy et al. |
| 6,316,504 B1 | 11/2001 | Youdim et al. |
| 6,462,222 B1 | 10/2002 | Chorev et al. |
| 6,548,706 B2 * | 4/2003 | Malik et al. ................. 564/483 |
| 6,630,514 B2 | 10/2003 | Youdim et al. |
| 6,956,060 B2 | 10/2005 | Youdim et al. |
| 7,396,860 B2 | 7/2008 | Blaugrund et al. |
| 7,491,847 B2 | 2/2009 | Frenkel |
| 7,547,806 B2 | 6/2009 | Frenkel et al. |
| 7,572,834 B1 | 8/2009 | Sterling et al. |
| 7,598,420 B1 | 10/2009 | Sterling et al. |
| 7,619,117 B1 | 11/2009 | Lidor-Hadas et al. |
| 7,750,051 B2 | 7/2010 | Frenkel et al. |
| 7,815,942 B2 | 10/2010 | Peskin |
| 2003/0180332 A1 | 9/2003 | Rimpler et al. |
| 2006/0018957 A1 | 1/2006 | Lerner et al. |
| 2006/0094783 A1 | 5/2006 | Youdim |
| 2006/0188581 A1 | 8/2006 | Peskin |
| 2007/0078172 A1 | 4/2007 | McElroy et al. |
| 2007/0093495 A1 | 4/2007 | Ruggero |
| 2007/0100001 A1 | 5/2007 | Youdim et al. |
| 2007/0112217 A1 | 5/2007 | Frenkel |
| 2007/0232700 A1 | 10/2007 | Blaugrund et al. |
| 2008/0161408 A1 | 7/2008 | Frenkel et al. |
| 2008/0208287 A1 | 8/2008 | Palermo et al. |
| 2008/0261894 A1 | 10/2008 | Kreitman et al. |
| 2009/0054504 A1 * | 2/2009 | Bozik et al. ................. 514/367 |
| 2009/0062400 A1 | 3/2009 | Oron et al. |
| 2009/0076160 A1 | 3/2009 | Lendvai et al. |
| 2009/0111892 A1 | 4/2009 | Patashnick et al. |
| 2009/0136549 A1 | 5/2009 | Lin et al. |
| 2009/0181086 A1 | 7/2009 | Safadi et al. |
| 2009/0220611 A1 | 9/2009 | Dargelas et al. |
| 2009/0247537 A1 | 10/2009 | Overfield |
| 2009/0312436 A1 | 12/2009 | Levy et al. |
| 2009/0318564 A1 | 12/2009 | Frenkel et al. |
| 2010/0008983 A1 | 1/2010 | Safadi et al. |
| 2010/0010095 A1 | 1/2010 | Frenkel |
| 2010/0010098 A1 | 1/2010 | Elffrink |
| 2010/0189787 A1 | 7/2010 | Safadi et al. |
| 2010/0189788 A1 | 7/2010 | Safadi et al. |
| 2010/0189790 A1 | 7/2010 | Safadi et al. |

(Continued)

FOREIGN PATENT DOCUMENTS

WO WO 95/11016 4/1995

(Continued)

OTHER PUBLICATIONS

Perrin et al. (Purification of Laboratory Chemicals Second Edition).*

(Continued)

*Primary Examiner*—Sreeni Padmanabhan
*Assistant Examiner*—Layla Soroush
(74) *Attorney, Agent, or Firm*—John P. White; Cooper & Dunham LLP

(57) ABSTRACT

The subject invention provides rasagiline citrate, its compositions and processes for the manufacture thereof.

16 Claims, No Drawings

U.S. PATENT DOCUMENTS

2010/0189791 A1     7/2010    Safadi et al.

FOREIGN PATENT DOCUMENTS

| WO | WO 98/40102 | 9/1998 |
| WO | WO 2004/089353 | 10/2004 |
| WO | WO 2006/014973 | 2/2006 |
| WO | WO 2006/057912 | 6/2006 |
| WO | WO 2008/076315 | 6/2006 |
| WO | WO 2007/10299 | 1/2007 |
| WO | WO 2007/060491 | 5/2007 |
| WO | WO 2008/010786 | 1/2008 |
| WO | WO 2008/019871 | 2/2008 |
| WO | WO 2008/076348 | 6/2008 |
| WO | WO 2008/131961 | 11/2008 |
| WO | WO 2008/139934 | 11/2008 |
| WO | WO 2009/122301 | 10/2009 |
| WO | WO 2009/152777 | 12/2009 |
| WO | PCT/EP2010/059723 | 7/2010 |

OTHER PUBLICATIONS

Chen et al. (Clinical Pharmacology of Rasagiline: A Novel, Second-Generation Propargylamine for the Treatment of Parkinson Disease).*

U.S. Appl. No. 12/456,642, filed Jun. 19, 2009 (Anton Frenkel) (specification and pending claim set is attached).

U.S. Appl. No. 12/456,643, filed Jun. 19, 2009 (Frenkel et al.) (specification and pending claim set is attached).

U.S. Appl. No. 12/455,969, filed Jun. 10, 2009 (Safadi et al..) (specification and pending claim set is attached).

U.S. Appl. No. 12/456,031, filed Jun. 9, 2009 (Safadi et al.) (specification and pending claim set is attached).

U.S. Appl. No. 12/456,029, filed Jun. 9, 2009 (Safadi et al.) (specification and pending claim set is attached).

U.S. Appl. No. 12/455,976, filed Jun. 9, 2009 (Safadi et al.) (specification and pending claim set is attached).

U.S. Appl. No. 12/456,001, filed Jun. 9, 2009 (Safadi et al.) (specification and pending claim set is attached).

Azilect®, Physician's Desk Reference (2009), 63th Edition, Thomson Healthcare.

Snodin D., (2006) "Residues of genotoxic alkyl mesylates in mesylate salt drug substances . . ." Regulatory Toxicology and Pharmacology, vol. 45, pp. 79-90.

U.S. Appl. No. 12/283,107, filed Sep. 8, 2008 (Sterling et al.) (specification and pending claim set is attached).

U.S. Appl. No. 12/223,794, filed Aug. 7, 2008 (Poewe) (specification and pending claim set is attached).

U.S. Appl. No. 12/456,166, filed Jun. 12, 2009 (Levy et al.) (specification and pending claim set is attached).

Mar. 16, 2010 International Search Report and the Written Opinion of the International Searching Authority for International Application No. PCT/US10/00174.

Jul. 28, 2000 Amendment filed in the U.S. Appl. No. 09/043,475.

May 2, 2000 Notice of Allowance issued in the U.S. Appl. No. 09/043,475.

Feb. 10, 2000 Amendment filed in the U.S. Appl. No. 09/043,475.

Nov. 10, 1999 Notice of Allowance issued in the U.S. Appl. No. 09/043,475.

Sep. 16, 1999 Amendment filed in the U.S. Appl. No. 09/043,475.

Jun. 16, 1999 Office Action issued in the U.S. Appl. No. 09/043,475.

Jul. 26, 2010 Extended European Search Report issued in European Patent Application No. 10151462.8.

"A Controlled Trial of Rasagiline . . . . The Tempo Study", Archives of Neurology, American Medical Association, Chicago, IL, US, vol. 59, Dec. 1, 2002, pp. 1937-1943.

Gould P. L, "Salt Selection for Basic Drugs", International Journal of Pharmaceutics, Elsevier BV, NL Lnkd-DOI:10.1016/0378-5173(86)90055-4, vol. 33, No. 1/03, January.

Feb. 12, 2009 Notice of Allowance issued in U.S. Appl. No. 12/002,076.

Jan. 12, 2009 Amendment filed in U.S. Appl. No. 12/007,076.

Jul. 11, 2008 Office Action issued in U.S. Appl. No. 12/002,076.

Sep. 30, 2010 Extended European Search Report issued in European Patent Application No. 10166534.7.

\* cited by examiner

CITRATE SALT OF RASAGILINE

The application claims benefit of U.S. Ser. No. 12/455,976, filed Jun. 9, 2009, and of U.S. Provisional Application No. 61/205,833, filed Jan. 23, 2009, the contents of each of which are hereby incorporated by reference.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

U.S. Pat. Nos. 5,532,415, 5,387,612, 5,453,446, 5,457,133, 5,599,991, 5,744,500, 5,891,923, 5,668,181, 5,576,353, 5,519,061, 5,786,390, 6,316,504, 6,630,514 disclose R(+)-N-propargyl-1-aminoindan ("R-PAI"), also known as rasagiline. U.S. Pat. No. 6,126,968 and PCT International Application Publication No. WO 95/11016 disclose pharmaceutical compositions comprising rasagiline. Rasagiline has been reported to be a selective inhibitor of the B-form of the enzyme monoamine oxidase ("MAO-B") and is useful in treating Parkinson's disease and various other conditions by inhibition of MAO-B in the brain.

A formulation of rasagiline mesylate is approved for treating Parkinson's disease either as monotherapy or as an adjunct with other treatments. See, e.g. AZILECT®, Physicians' Desk Reference 2009 (PRD, 63$^{rd}$ Edition).

AZILECT® is indicated for the treatment of the signs and symptoms of idiopathic Parkinson's disease as initial monotherapy and as adjunct therapy to levodopa. Rasagiline, the active ingredient of AZILECT®, is rapidly absorbed, reaching peak plasma concentration ($C_{max}$) in approximately 1 hour. The absolute bioavailability of rasagiline is about (AZILECT® Product Label, May 2006).

There are, however, several concerns associated with the commercially available form of rasagiline mesylate. For example, a concern with the use of monoamine oxidase ("MAO") inhibitors is the risk of hypertensive crises, often called the "cheese effect." (Simpson, G. M. and White K. "Tyramine studies and the safety of MAOI drugs." J Clin Psychiatry. 1984 July; 45 (7 pt 2): 59-91.) Such an effect is caused by inhibition of peripheral MAO. A high concentration of peripheral MAO is found in the stomach.

Another concern in Parkinson's disease patients is that many patients suffer from delayed gastric emptying (Pfeiffer, R. F. and Quigley, E. M. M. "Gastrointestinal motility problems in patients with Parkinson's disease: Epidemiology, pathophysiology, and guidelines for management," CNS-Drugs, 1999, 11(6): 435-448; Jost, W. H., "Gastrointestinal motility problems in patients with Parkinson's disease: Effects of antiparkinsonian treatment and guidelines for management", Drugs and Aging, 1997, 10(4): 249-258). Delayed gastric emptying (prolonged gastric residence) can be a cause of increased inhibition of peripheral MAO, and can contribute to the cheese effect.

There is also a concern regarding the potential for formation of alkyl mesylates during the treatment of the free base of a drug substance with methane sulfonic acid if any residues of short-chain alcohols are present. (Snodin D., "Residues of genotoxic alkyl mesylates in mesylate salt drug substances: Real or imaginary problems?" *Regulatory Toxicology and Pharmacology*, Vol. 45, 2006, pages 79-90).

Efforts to address such concerns and to improve the commercially available form of rasagiline mesylate are described in the literature. For example, PCT International Application Publication No. WO 2006/057912 describes orally disintegrating rasagiline compositions; PCT International Application Publication No. WO 2006/014973 discloses delayed release rasagiline compositions; PCT International Application Publication No. WO 2008/076348 discloses a crystalline solid form of the rasagiline base; PCT International Application Publication No. WO 2008/076315 discloses the tannate salt of rasagiline. Other efforts to make certain improvements are described in PCT International Application Publication No. WO 2008/019871 and in PCT International Application Publication No. WO 2008/131961.

However, the previous efforts did not disclose the citrate salt of rasagiline or the advantages of the citrate salt of rasagiline, described herein.

SUMMARY OF THE INVENTION

The subject invention provides rasagiline citrate.

The subject invention also provides a composition comprising the rasagiline citrate described herein and a carrier.

The subject invention further provides a process for manufacture of the rasagiline citrate or the composition describe herein, comprising:
a) combining a solution of citric acid with rasagiline base to form a first mixture;
b) adding a solvent to the first mixture to form a second mixture;
c) completely removing liquid from the second mixture; and
d) recovering the rasagiline citrate or preparing the composition.

The subject invention yet further provides a process for manufacture of the composition described herein, comprising:
a) obtaining rasagiline citrate in isolated form; and
b) admixing the rasagiline citrate with a carrier.

The subject invention yet further provides a method of treating a human subject afflicted with Parkinson's disease (PD), brain ischemia, stroke, head trauma injury, spinal trauma injury, neurotrauma, neurodegenerative disease, neurotoxic injury, nerve damage, dementia, Alzheimer's type dementia, senile dementia, depression, memory disorders, hyperactive syndrome, attention deficit disorder, Multiple Sclerosis (MS), schizophrenia, affective illness, Amyotrophic Lateral Sclerosis, Restless Legs Syndrome (RLS), hearing loss, Multiple System Atrophy (MSA), Glucoma, modifying Parkinson's disease, and Progressive Supranuclear Palsy (PSP), comprising administering to the human subject an amount of the rasagiline citrate or the composition described herein effective to treat the human subject.

DETAILED DESCRIPTION OF THE INVENTION

The subject invention provides rasagiline citrate.

In an embodiment of the rasagiline citrate, the rasagiline citrate is isolated rasagiline citrate or is substantially pure.

In another embodiment of the rasagiline citrate described herein, the rasagiline citrate is amorphous.

In yet another embodiment of the rasagiline citrate described herein, the rasagiline citrate is mono-rasagiline citrate.

In yet another embodiment of the rasagiline citrate described herein, the rasagiline content in the rasagiline citrate is between 42% and 52% by weight based on the total weight of the rasagiline citrate.

By a range between 42% and 52%, it is meant that all tenth and integer percentages within the range are specifically disclosed as part of the invention. Thus, 43%, 44%, ..., 50%, 51% and 42.1%, 42.2%, ..., 51.8%, 51.9% are included as embodiments of this invention.

In yet another embodiment of the rasagiline citrate described herein, the water content in the rasagiline citrate as determined by Karl Fischer analysis is less than 5%, less than 4%, less than 3%, less than 2%, or less than 1%.

The subject invention also provides a composition comprising the rasagiline citrate described herein and a carrier.

In an embodiment of the composition, the composition further comprises rasagiline base.

In another embodiment of the composition described herein, the rasagiline base is present in an amount of less than 5%, less than 4%, less than 3%, less than 2%, or less than 1%, based on the total rasagiline content of the composition.

In yet another embodiment of the composition described herein, the rasagiline base present in the composition is crystalline rasagiline base.

In yet another embodiment of the composition described herein, the composition is free of rasagiline base.

In yet another embodiment of the composition described herein, the rasagiline content present in the form of rasagiline citrate is more than 50%, 60%, 70%, 80%, 90%, 95%, 96%, 97%, 98%, or 99% of the total rasagiline content in the composition.

In yet another embodiment of the composition described herein, the composition is a pharmaceutical composition and the carrier is a pharmaceutically acceptable carrier.

In yet another embodiment of the composition described herein, the composition is in the form of an oral dosage form.

In yet another embodiment of the composition described herein, the composition is in the form of a tablet.

In yet another embodiment of the composition described herein, the composition further comprises stearic acid.

In yet another embodiment of the composition described herein, the composition is in the form of a transdermal patch.

In yet another embodiment of the composition described herein, the rasagiline citrate is mixed with a polymer.

The subject invention further provides a process for manufacture of the rasagiline citrate or the composition described herein, comprising:
a) combining a solution of citric acid with rasagiline base to form a first mixture;
b) adding a solvent to the first mixture to form a second mixture;
c) completely removing liquid from the second mixture; and
d) recovering the rasagiline citrate or preparing the composition.

In an embodiment of the process, the solvent added in step b) is acetone.

In another embodiment of the process described herein, in step c) the liquid is removed at ambient temperature and at reduced pressure.

The subject invention yet further provides a process for manufacture of the composition described herein, comprising:
a) obtaining rasagiline citrate in isolated form; and
b) admixing the rasagiline citrate with a carrier.

The subject invention yet further provides a method of treating a human subject afflicted with Parkinson's disease (PD), brain ischemia, stroke, head trauma injury, spinal trauma injury, neurotrauma, neurodegenerative disease, neurotoxic injury, nerve damage, dementia, Alzheimer's type dementia, senile dementia, depression, memory disorders, hyperactive syndrome, attention deficit disorder, Multiple Sclerosis (MS), schizophrenia, affective illness, Amyotrophic Lateral Sclerosis, Restless Legs Syndrome (RLS), hearing loss, Multiple System Atrophy (MSA), Glucoma, modifying Parkinson's disease, and Progressive Supranuclear Palsy (PSP), comprising administering to the human subject an amount of the rasagiline citrate or the composition described herein effective to treat the human subject.

Each of the embodiments described herein can be combined with any other embodiment disclosed herein.

By any range disclosed herein, it is meant that all hundredth, tenth and integer unit amounts within the range are specifically disclosed as part of the invention. Thus, for example, 0.01 mg to 50 mg means that 0.02, 0.03 ... 0.09; 0.1, 0.2 ... 0.9; and 1, 2 ... 49 mg unit amounts are included as embodiments of this invention.

Citric acid is a weak organic acid, and is triprotic. Therefore, the rasagiline citrate described herein may exist in mono-, di- or tri-rasagiline citrate form or a mixture thereof.

As used herein, an example of an immediate release formulation of rasagiline is an AZILECT® tablet containing rasagiline mesylate.

As used herein, a polymer is a large molecule composed of repeating structural units typically connected by covalent chemical bonds.

In all of its aspects, the present invention provides pharmaceutical dosage forms useful for treating a condition selected from the group consisting of: Parkinson's disease (PD), brain ischemia, stroke, head trauma injury, spinal trauma injury, neurotrauma, neurodegenerative disease, neurotoxic injury, nerve damage, dementia, Alzheimer's type dementia, senile dementia, depression, memory disorders, hyperactive syndrome, attention deficit disorder, Multiple Sclerosis (MS), schizophrenia, affective illness, Amyotrophic Lateral Sclerosis, Restless Legs Syndrome (RLS), hearing loss, Multiple System Atrophy (MSA), Glucoma, modifying Parkinson's disease, and Progressive Supranuclear Palsy (PSP), but with a reduced risk of peripheral MAO inhibition that is typically associated with administration of rasagiline with known oral dosage forms.

As used herein, a "pharmaceutically acceptable" carrier or excipient is one that is suitable for use with humans and/or animals without undue adverse side effects (such as toxicity, irritation, and allergic response) commensurate with a reasonable benefit/risk ratio.

Specific examples of pharmaceutically acceptable carriers and excipients that may be used to formulate oral dosage forms of the present invention are described, e.g., in U.S. Pat. No. 6,126,968 to Peskin et al., issued Oct. 3, 2000. Techniques and compositions for making dosage forms useful in the present invention are described, for example, in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The pharmaceutical dosage forms may be prepared as medicaments to be administered orally, parenterally, rectally or transdermally. Suitable forms for oral administration include tablets, compressed or coated pills, dragees, sachets, hard or soft gelatin capsules, sublingual tablets, syrups and suspensions; for parenteral administration the invention provides ampoules or vials that include an aqueous or non-aqueous solution or emulsion; for rectal administration the invention provides suppositories with hydrophilic or hydrophobic vehicles; for topical application as ointments; and for transdermal delivery the invention provides suitable delivery systems as known in the art.

Tablets may contain suitable binders, lubricants, disintegrating agents, coloring agents, flavoring agents, flow-inducing agents, melting agents, stabilizing agents, solubilizing agents, antioxidants, buffering agent, chelating agents, fillers and plasticizers. For instance, for oral administration in the dosage unit form of a tablet or capsule, the active drug component can be combined with an oral, non-toxic, pharmaceutically acceptable, inert carrier such as gelatin, agar, starch, methyl cellulose, dicalcium phosphate, calcium sulfate, mannitol, sorbitol, microcrystalline cellulose and the like. Suitable binders include starch, gelatin, natural sugars such as corn starch, natural and synthetic gums such as acacia, tragacanth, or sodium alginate, povidone, carboxymethylcellulose, polyethylene glycol, waxes, and the like. Antioxidants include ascorbic acid, fumaric acid, citric acid, malic acid, gallic acid and its salts and esters, butylated hydroxyanisole, editic acid. Lubricants used in these dosage forms include sodium oleate, sodium stearate, sodium benzoate, sodium acetate, stearic acid, sodium stearyl fumarate, talc and the like. Disintegrators include, without limitation, starch, methyl cellulose, agar, bentonite, xanthan gum, croscarmellose sodium, sodium starch glycolate and the like, suitable plasticizers include triacetin, triethyl citrate, dibutyl sebacate, polyethylene glycol and the like.

One type of oral dosage forms of the present invention relates to delayed release formulations. Such formulations may be comprised of an acid resistant excipient which prevents the dosage form or parts thereof from contacting the acidic environment of the stomach. The acid resistant excipient may coat the rasagiline in the form of an enteric coated tablet, capsule, or gelatin capsule. Enteric coating, in the context of this invention, is a coating which prevents the dissolution of an active ingredient in the stomach. Specific examples of pharmaceutically acceptable carriers and excipients that may be used to formulate such delayed release formulations are described, e.g., in International Application Publication No. WO 06/014973, hereby incorporated by reference in its entirety.

Another type of oral dosage forms of the present invention relates to fast disintegrating formulations which provide a means to avoid the absorption of rasagiline in the stomach, and to eliminate the need for swallowing tablets, by absorption of rasagiline into the body before reaching the stomach. Such absorption of rasagiline can be accomplished by contact with the buccal, sublingual, pharyngeal and/or esophageal mucous membranes. To accomplish this, the fast disintegrating formulations were designed to rapidly disperse within the mouth to allow maximum contact of rasagiline with the buccal, sublingual, pharyngeal and/or esophageal mucous membranes. Specific examples of pharmaceutically acceptable carriers and excipients that may be used to formulate such fast disintegrating formulations are described, e.g., in International Application Publication No. WO 03/051338, hereby incorporated by reference in its entirety.

Other pharmaceutical compositions of the present invention include transdermal patches. Transdermal patches are medicated adhesive patches placed on the skin to deliver a time-released dose of medication through the skin and into the bloodstream. A wide variety of pharmaceuticals can be delivered through transdermal patches. Some pharmaceuticals must be combined with other substances, for example alcohol, to increase their ability to penetrate the skin. Transdermal patches have several important components, including a liner to protect the patch during storage, the drug, adhesive, a membrane (to control release of the drug from the reservoir), and a backing to protect the patch from the outer environment. The two most common types of transdermal patches are matrix and reservoir types. (Wikipedia; and Remington, The Science and Practice of Pharmacy, $20^{th}$ Edition, 2000)

In reservoir type patches, a drug is combined with a non-volatile, inert liquid, such as mineral oil, whereas in matrix type patches a drug is dispersed in a lipophilic or hydrophilic polymer matrix such as acrylic or vinylic polymers. Adhesive polymers, such as polyisobutylene, are used to hold the patch in place on the skin. (Stanley Scheindlin, (2004) "Transdermal Drug Delivery: PAST, PRESENT, FUTURE," Molecular Interventions, 4:308-312)

The major limitation to transdermal drug-delivery is the intrinsic barrier property of the skin. Penetration enhancers are often added to transdermal drug formulations in order to disrupt the skin surface and cause faster drug delivery. Typical penetration enhancers include high-boiling alcohols, diols, fatty acid esters, oleic acid and glyceride-based solvents, and are commonly added at a concentration of one to 20 percent (w/w). (Melinda Hopp, "Developing Custom Adhesive Systems for Transdermal Drug Delivery Products," Drug Delivery)

As used herein, an "isolated" compound is a compound that has been separated from the crude reaction mixture in which it formed by an affirmative act of isolation. The act of isolation necessarily involves separating the compound from the other known components of the crude reaction mixture, with some impurities, unknown side products and residual amounts of the other known components of the crude reaction mixture permitted to remain. Purification is an example of an affirmative act of isolation.

As used herein, a composition that is "free" of a chemical entity means that the composition contains, if at all, an amount of the chemical entity which cannot be avoided following an affirmative act intended to separate the chemical entity and the composition.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art or by processes analogous to those described in the Examples disclosed herein using an appropriate isotopically-labeled reagents in place of the non-labeled reagents employed.

This invention will be better understood from the experimental details which follow. However, one skilled in the art will readily appreciate that the specific methods and results discussed are merely illustrative of the invention as described more fully in the claims which follow thereafter.

EXPERIMENTAL DETAILS

MAO inhibitors that selectively inhibit MAO-B are largely devoid of the potential to cause the "cheese effect". Nonetheless, the possibility exists that delayed gastric emptying of R-PAI may contribute to this phenomenon. Therefore, an effort was undertaken to develop a delayed release, enteric coated formulation comprising rasagiline in an amount equivalent to 1 mg of rasagiline base which would release the active ingredient in the duodenum and the jejunum, past the stomach. More specifically, formulations were developed that meet the criteria of bioequivalence to the known, immediate release rasagiline mesylate formulations (as disclosed in example 1) in a single dose bio-equivalence study in healthy subjects. These criteria include similarity of $C_{max}$ and $AUC_{0-t}$ (area under the curve) within the range of 80-125% within a 90% confidence interval between the new formulations and the known, immediate release formulations. The difference between the two formulations should be evident in bioequivalence studies as a difference in $t_{max}$. In other words, the mean pharmacokinetic profile of the formulations matches the mean pharmacokinetic profile of the formulations of the known immediate release formulation, with the exception of the $t_{max}$ which should be greater for the delayed release formulation than for the immediate release formulation.

During the course of this development, it was discovered that the formulation according to Example 3 below resulted in in situ formation of a new salt form of rasagiline, namely rasagiline citrate. Efforts were then directed to preparing and characterizing this new salt form and in particular to determining whether this new salt form contributed to the advantageous properties of the formulation. The properties of this new salt form include unexpected properties, as discussed throughout the Examples following Example 3.

Example 1

Rasagiline Immediate Release Tablets

Rasagiline immediate release tablets were prepared using the ingredients listed in Table 1.

TABLE 1

| Component | Function | Per Tablet (mg) (0.5 mg Rasagiline base) | Per Tablet (mg) (1 mg Rasagiline base) |
| --- | --- | --- | --- |
| Rasagiline mesylate | | 0.78 | 1.56 |
| Mannitol | Filler | 79.62 | 159.24 |
| Aerosil | Flowing Agent | 0.6 | 1.2 |
| Starch NF | Binder | 10.0 | 20.0 |
| Starch, Pregelatinized | Disintegrant | 10.0 | 20.0 |
| (Starch STA-RX 1500) | | | |
| Talc | Lubricant | 2.0 | 4.0 |
| Stearic Acid | Lubricant | 2.0 | 4.0 |
| Total core Tablet Weight | | 105 | 210 |

Rasagiline mesylate, mannitol, half of the colloidal silicon dioxide, starch and pregelatinized starch were mixed in a Diosna P-800 mixer for about 5 minutes. Water was added and the mixture was mixed further. The granulate was dried and the remainder of the colloidal silicon dioxide was added. The granulate was ground in a Frewitt mill and stearic acid and talc were added. The resulting mixture was mixed for five minutes in a tumbler and was then tableted.

Example 2

Preparation of Crystalline Rasagiline Base

A process for preparing crystalline rasagiline base is disclosed in U.S. Patent Application Publication No. 2008/0161408 (and which corresponds to WO 2008/076348). In particular, the document describes a process for manufacture of crystalline rasagiline base which comprises: a) dissolving a salt of R(+)-N-propargyl-1-aminoindan in water to form a solution; b) cooling the solution to a temperature of about 0-15° C.; c) basifying the solution to a pH of about 11 to form a suspension; and d) obtaining the crystalline rasagiline base from the suspension.

Solid crystalline rasagiline base used in the following examples was prepared in a similar process as follows:

A) Preparation of Rasagiline Base Oil 100.0 g of Rasagiline Tartrate was suspended in 458 ml deionized water, 229 ml Toluene was added and 46 ml of 25% NaOH solution was introduced at stirring. The mixture was heated to 45° C., stirred at 45 C for 15 minutes and settled at this temperature.

Two phases were separated. The lower aqueous phase (pH=13-14) was discarded, the upper toluenic phase was washed with 140 ml deionized water. The resulting emulsion was settled, and two phases were separated. The lower aqueous phase (pH=9-10) was discarded. The toluenic solution was evaporated under vacuum in evaporator.

After the solvent evaporation completion 60 ml isopropanol was added to the residue and evaporation was continued.

After completion of the evaporation 50 ml of isopropanol was added and distilled out under the same conditions.

The residue, oil of R-PAI base, was obtained.

B) Crystallization of Rasagiline Base

The rasagiline base oil obtained in step A) above was dissolved in 56 ml isopropanol.

The solution was cooled to 16° C. and 147.5 ml of deionized water was added by portions in 3 hr at cooling and stirring. During the addition of water precipitation development was observed and the batch was immediately seeded with crystalline R-PAI base.

The resulting suspension was cooled to 2° C., stirred at this temperature overnight and filtered. The solid was washed with water and dried at room temperature under vacuum.

Solid dry R-PAI base were obtained, with a yield of 96% relative to oil base.

Example 3

Preparation of Delayed Release Enteric Coated Tablet

Rasagiline citrate was identified as having been formed in the tablet which was prepared as described below.

Composition of rasagiline base delayed release enteric coated tablet

| Ingredient | mg/tab | Percentage of total weight |
|---|---|---|
| Mannitol | 79.84 | 60.3 |
| Citric Acid | 1.6 | 1.2 |
| Colloidal Silicon Dioxide | 0.6 | 0.453 |
| Rasagiline Base | 1 | 0.755 |
| Starch NF | 10.0 | 7.55 |
| Pregelatinized Starch (STA-RX ® 1500) | 20.0 | 15.1 |
| Stearic Acid | 2.0 | 1.51 |
| Talc | 2.0 | 1.51 |
| Hypromellose (Pharmacoat ® 606G) | 4.8 | 3.625 |
| Methacrylic Acid Ethyl Acrylate copolymer (Eudragit ® L 100-55) | 6.250 | 4.72 |
| Triethyl citrate | 1.25 | 0.944 |
| Talc DSP Extra Fine | 3.1 | 2.34 |

I. Dry Mixing:

Mannitol, Aerosil, Pregelatinized Starch and Starch NF were placed in a high shear granulating mixer and premixed for 1 minute at mixer speed I, followed by 1 minute at mixer speed II and chopper II.

II. Wet Granulation:

Citric acid solution was prepared using 320 g of citric acid, dissolved in 3000 g purified water. Rasagiline Base was added to the citric acid solution with stirring over 15 minutes. The solution was then added to the mixture from Step I in the high shear granulating mixer and the content was mixed for 2 minute at mixer speed II and chopper II.

The wet granulate was then discharged to a fluid bed dryer trolley at mixer speed I.

III. Fluid Bed Drying:

The material from Step II was dried in a fluid bed dryer under inlet air temperature of 45° C. (40° to 50° C.) and outlet air temperature of maximum 37° C.

A small amount of the dried granulate was passed through Frewitt with a 0.6 mm screen and the Loss-On-Drying (L.O.D.) was determined.

The L.O.D. result was as follows:

| L.O.D. | 1.4% |
|---|---|

IV. Milling:

The dry granulate from Step III was milled through an oscillating granulator with screen 0.6 mm into a storage container.

The milled granulate was weighed and a yield of 95.2% was obtained.

V. Final Blending:

Stearic Acid and Talc were sieved through a 50 mesh screen and were transferred to a Y-cone 50.
1. The mixture was mixed for 5 minutes.
2. The final blend was obtained and the percentage yield was determined to be 99.1%.
3. The final blend was stored in a container using an inner transparent polyethylene bag and an outer black polyethylene bag. Two Silica gel pillows were placed between the two polyethylene bags.
4. Samples were taken for a Blend Uniformity test.

VI. Tablet Compression:

The tablet machine (FETTE 1200) was set up with the designated punches 0160 (6.0 mm).

The in-process control testing for tablets included average weight, individual weight, thickness, hardness, friability and disintegration.

In process control specifications for Rasagiline Base DR 1 mg tablets is:

| Parameter | Minimum | Target | Maximum |
|---|---|---|---|
| Average weight (mg) | 111 | 117 | 123 |
| Individual weight (mg) | 111 | 117 | 123 |
| Thickness (mm) | 3.3 | 3.6 | 3.9 |
| Hardness (SCU) | 7 | 9 | 11 |
| Friability (%) | — | — | 1.0 |
| Disintegration (min.) | — | — | 2 |

The tablet cores prepared were weighed and the percentage yield was calculated.

VII. Sub-Coating:

Tablet cores from Step VI were first coated with hypromellose (Pharmacoat 606G®) as a pre-coating, followed by Methacrylic Acid-Methyl Methacrylate Copolymer [1:1] (30% dispersion of Eudragit® L100-55) to prevent any possible interaction between the Rasagiline base in the core and the Eudragit L polymer.

1. Preparation of Pharmacoat 606G® solution: Hypromellose USP solution was prepared using 1000 g of hypromellose, in 9677 g purified water.
2. Pre-heating: The tablet cores were placed in an Ohara Coater coating pan. The tablet cores were heated under inlet air temperature of 50° C. (45° to 55° C.) and outlet air temperature of 37° C. (45° to 55° C.)
3. Spraying process: The tablet cores were sprayed with hypromellose solution in the Ohara Coater coating pan. The inlet air temperature was 40° C.; the outlet air temperature was in range of 30° C.-35° C. The pan speed was set to 10 rpm. Spraying rate was 10-20 gr/min. The sub-coated tablets were dried for 2 hours with inlet air temperature of 40° C.

VIII. Enteric Coating:

1. Preparation of 30% dispersion of Eudragit® L100-55 solution: Triethyl citrate was mixed with water for 15 min. The Talc Extra fine was added into the Triethyl citrate and water dispersion in an Ultraturax within 10 minutes. Eudragit L100-55 solution was added to Triethyl citrate/talc dispersion. Agitation of the dispersion was maintained throughout the entire coating process.
2. Spraying process: the sub-coated tablets from Step VII were sprayed with the dispersion in an Ohara coater pan.

The inlet air temperature was 45° C. the outlet air temperature was in range of 30-35° C. The pan speed was set to 16 rpm, and the spraying rate was 10-20 gr/min. The coated tablets were dried for 2 hours; with inlet air temperature was 40° C., on minimum pan speed.

EUDRAGIT® L 100-55 contains an anionic copolymer based on methacrylic acid and ethyl acrylate. It is also known as methacrylic acid copolymer, type C. The ratio of the free carboxyl groups to the ester groups is approx. 1:1. The average molecular weight is approx. 250,000.

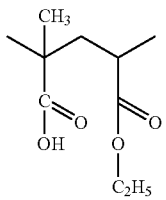

Example 4

Preparation of Rasagiline Citrate

This example describes the preparation and characterization of rasagiline citrate salt. Rasagiline citrate is an attractive drug substance. Since citric acid is a tribasic compound, there are three possible forms of rasagiline citrate: mono-, di- and tri-citrate. Therefore, Rasagiline citrate described herein can be mono-rasagiline citrate, di-rasagiline citrate, or tri-rasagiline citrate, or a mixture thereof.

Because rasagiline is a weak base and $pK_a$ values of citric acid are 3.13, 4.76 and 6.40, it can be assumed that bonding of $1^{st}$ and $2^{nd}$ rasagiline base molecules to citrate is much more probable than bonding of the $3^{rd}$ rasagiline base molecule.

Starting Materials

Citric acid—anhydrous acid of USP grade was used for preparation of citrate salts.

Rasagiline base—crystalline Rasagiline base prepared according to Example 2 was used in this study.

Example 4a

Preparation of Rasagiline Citrate in Ethanol-Acetone 3.02 g of Citric acid was dissolved in 10 ml absolute ethanol at room temperature. 5.38 g rasagiline base was dissolved in 15 ml absolute ethanol. Solution of rasagiline base was introduced by portions into the solution of citric acid under stirring. Significant exothermal effect was recorded during the addition, during which the solution temperature rose from 17° to 24° C. during 10 minutes of addition. The resulting clear solution was stored in freezer at −18° C. and no precipitation was observed.

Additional 2.71 g of solid Rasagiline base was added to the above resulting clear solution. After prolonged stirring at 20-23° C. the solid was dissolved and a viscous clear solution was obtained. The resulting viscous clear solution was stored overnight in freezer at −18° C. No solid precipitation from the solution was observed during 20 hrs in the freezer.

The solution was evaporated under vacuum on rotary evaporator, the resulted residue (11.2 g) of honey-like semi-solid material was held over weekend in freezer (−18° C.). No crystallization of solid was observed.

The semi-solid material was mixed with 40 ml acetone at stirring, no dissolution of the semi-solid material was observed during prolonged stirring.

Absolute ethanol (3 ml) was then added to the mixture by portions at stirring. Complete dissolution of the semi-solid material was observed, the resulting clear solution was held overnight in freezer.

Honey-like semi-solid material precipitated from the acetone-ethanol solution was found on the bottom of the flask. The solution was decanted and the precipitate was dried under vacuum (20 mbar) for 4 hours. During the drying a stabile foam formed. The flask with the foam was connected to high vacuum pump and dried at 2-3 mbar overnight.

The foam solidified under high vacuum. The vacuum was disconnected and the material was broken up with spatula. 6.1 g of white powder was obtained.

Analysis:
Assay of Rasagiline base by HPLC—60.8%
Crystallinity by XRD—Amorphous
Thermal Analysis:
DSC—Peak at 179.7° C. (128 exo), TGA—LOD=1.2% (25-100° C.), cont. weight loss at T>100° C.

Example 4b

Mono-Citrate Salt in Water-Acetone (Molar Ratio 1:1)

3.02 g of Citric acid was dissolved in 4 ml deionized water. 2.69 g of Rasagiline base was added to the solution. Exothermic effect was observed (temperature rose from 22 to 25° C.), and most of the solid was dissolved. Then the mixture was heated to 42° and complete dissolution of the solid was observed. The resulting clear viscous syrup-like solution was held in refrigerator at +5° C. overnight. No precipitation was observed during 15 hrs.

The solution was mixed with 15 ml acetone and evaporated on rotary evaporator under vacuum. The residue of honey-like semi-solid material (6.29 g) was dried under vacuum (20 mbar) at ambient temperature. A foam formed (6.11 g) during the drying and then further dried under high vacuum (2-3 mbar).

The foam was solidified under high vacuum. The vacuum was disconnected and the material was broken up with spatula. 5.58 g of white powder was obtained.

Analysis:
Assay of Rasagiline base by HPLC—44.5%
Crystallinity by XRD—Amorphous
Thermal Analysis:
DSC—Peak at 188.6° C. (61 exo), TGA—LOD=1.5% (25-100° C.), cont. weight loss at T>100° C.

Example 4c

Di-Citrate Salt in Water-Acetone (Molar Ratio 2:1)

3.45 g of Citric acid was dissolved in 5 ml deionized water and pre-heated to 30° C. 6.13 g of Rasagiline base was added to the solution. Exothermic effect was observed (temperature rose from 30 to 36° C.), and the solid was dissolved. The resulted clear viscous syrup-like solution was held in refrigerator at +5° C. overnight. No precipitation was observed during 15 hrs.

The solution was mixed with 18 ml acetone and evaporated on rotary evaporator under vacuum. The residue of honey-like semi-solid material (9.7 g) was dried under vacuum (20 mbar)

at ambient temperature. A foam formed during the drying and then further dried under high vacuum (2-3 mbar).

The foam was solidified under high vacuum. The vacuum was disconnected and the material was broken up with spatula. 8.81 g of white powder was obtained.

Analysis:
Assay of Rasagiline base by HPLC—60.9%
Crystallinity by XRD—Amorphous
Thermal Analysis:
DSC—Peak at 180.2° C. (141 exo), TGA—LOD=1.2% (25-100° C.), cont. weight loss at T>100° C.

Example 4d

Tri-Citrate Salt in Water-Acetone (Molar Ratio 3:1)

3.46 g of Citric acid was dissolved in 5 ml deionized water. 9.19 g of Rasagiline base was added to the solution. Exothermic effect was observed (temperature rose from 22 to 27° C.), and most of the solid was dissolved. Then the mixture was heated to 46° C. 0.5 ml water was added and complete dissolution of the solid was observed. The resulting clear viscous syrup-like solution was held in refrigerator at +5° C. overnight. No precipitation was observed during 15 hrs.

The solution was mixed with 18 ml acetone and evaporated on rotary evaporator under vacuum. The residue of honey-like semi-solid material (13.20 g) was dried under vacuum (20 mbar) at ambient temperature. A foam formed during the drying (13.19 g) and then further dried under high vacuum (2-3 mbar).

The foam was solidified under high vacuum. The vacuum was disconnected and the material was broken up with spatula. 12.80 g of white powder was obtained.

Analysis:
Assay of Rasagiline base by HPLC—70.6%
Crystallinity by XRD—Amorphous
Thermal Analysis:
DSC—Peak at 181.8° C. (136 exo), TGA—LOD=1.3% (25-100° C.), weight loss at T>100° C.

Discussion of Example 4

Experimental observations show exothermic reactions between Rasagiline base and Citric acid in aqueous solutions. The fact that Rasagiline base with aqueous solubility of about 2 mg/ml dissolves in aqueous reaction solution at more than 10 wt % demonstrates complete or near-complete conversion of the base into salt.

At the same time a fraction of the base could be extracted from the salt solution with non-polar organic solvent as toluene.

The preparation of mono-, di- and tri-citrate salts of rasagiline can be calculated from molecular weights of Rasagiline (R-PAI), Citric acid and water. The calculation results are presented in Table 4a below. The data presented in Table 4a also demonstrate that R-PAI content in the citrates prepared in the Examples 4a-4d conforms to the composition of hydrate salts.

TABLE 4a

Rasagiline Citrates calculated composition

| Salt | Composition | MW | R-PAI content % wt. | Water content % wt. |
|---|---|---|---|---|
| Mono-Citrate | $(R\text{-}PAIH^+)CitH_2^-$ | 363.3 | 47.1 | 0 |
| Di-Citrate | $(R\text{-}PAIH^+)_2CitH^{-2}$ | 534.5 | 64.0 | 0 |
| Tri-Citrate | $(R\text{-}PAIH^+)_3Cit^{-3}$ | 705.7 | 72.8 | 0 |
| Mono-Citrate monohydrate | $(R\text{-}PAIH^+)CitH_2^- \cdot H_2O$ | 381.3 | 44.9 | 4.7 |
| Di-Citrate monohydrate | $(R\text{-}PAIH^+)_2CitH^{-2} \cdot H_2O$ | 552.5 | 61.9 | 3.2 |
| Tri-Citrate monohydrate | $(R\text{-}PAIH^+)_3Cit^{-3} \cdot H_2O$ | 723.7 | 70.9 | 2.5 |
| Di-Citrate dihydrate | $(R\text{-}PAIH^+)_2CitH^{-2} \cdot 2H_2O$ | 570.5 | 60.0 | 3.1 |

$R\text{-}PAIH^+$—Rasagiline base (R-PAI) cation
$Cit^{-n}$—Citrate anion

Rasagiline citrate salts prepared in Examples 4a-4d demonstrate extremely high aqueous solubility. Solutions of mono- di- and tricitrate salts prepared in the Examples 4b, 4c and 4d had concentrations of dissolved solid of 59, 66 and 70 wt %, respectively. These solutions did not show saturation and were found stable at low temperatures. No precipitation was observed during 15 hrs at +5° C. This data shows extremely high solubility of the citrate salts of rasagiline in water. Solutions with more than 70% wt of rasagiline citrate could be prepared. Rasagiline citrate salts having 3-10 wt % water content appear as syrups or honey-like semi-solid.

The most soluble rasagiline salt described previously is monobasic maleate salt of rasagiline, which has a solubility not less than 1000 mg/ml water, as described in U.S. Pat. No. 6,630,514. But the phenomenon of extremely high solubility exhibited by rasagiline citrate was not observed in any previously identified salt of rasagiline.

Such extremely high solubility is a property of practical value, and allows for preparation of highly concentrated liquid and semi-solid formulations. Aqueous or alcoholic solution of Rasagiline Citrate containing 60-80% of active pharmaceutical ingredient (API) could be used in the production of transdermal patches, sublingual strips, and other formulations benefiting from such highly concentrated liquid or semi-solid. Such highly concentrated solutions are also useful for optimizing the efficiency of production processes, e.g. for tablets.

Example 5

Additional Preparation of Rasagiline Citrate

This example describes the additional preparation and characterization of rasagiline citrate salt.

Starting Materials

Citric acid—anhydrous acid of USP grade was used for preparation of Citrate salts.

Rasagiline base—pure crystalline Rasagiline base (DS) prepared according to Example 2 was used in this study.

Example 5.1

3.84 g of citric acid was dissolved in 25 ml water and 3.42 g of rasagiline base was added to the solution, which was stirred at room temperature and monitored by TLC. After 30 minutes no traces of R-PAI was observed on TLC. The reaction mixture was extracted with 2×30 ml toluene after one hour. The combined toluenic extract was evaporated to dryness. Yield: 0.06 g (1.75%) (R-PAI).

The aqueous phase was evaporated in vacuum to dryness. Honey-like semi-solid product was obtained. Yield: 7.53 g (103.7%).

Example 5.2

1.92 g of citric acid was dissolved in 10 ml water and 1.71 g of rasagiline base added to the solution. The mixture was stirred for 18 hours and then the solvent was removed by lyophilization (1-0.3 mbar; −20-+20° C.; 46 hours). Yield: 3.69 g (101.65%).

The product was solid foam but after several hours became a semi-solid honey-like material. According to NMR data the salt formed with 0.73 equivalent of acid.

Example 5.3

1.92 g of citric acid was dissolved in 15 ml water and 3.42 g of rasagiline base was added to the solution. The reaction mixture was stirred at room temperature for 22 hours. The water was removed by lyophilization (1-0.3 mbar, −20-+20° C.; 46 hours).

Crystalline-like foam were obtained, which then became semi-solid honey-like material in a few hours. According to the data of NMR the salt formed with 0.48 equivalent of acid.

Example 5.4

3.84 g of citric acid was dissolved in 30 ml water and 6.84 g of rasagiline base was added to the solution, which was stirred for 2 hours and then the reaction mixture was extracted with 2×40 ml toluene. The combined toluenic extract was evaporated to dryness. 20 ml IPA was added to the residue and the solvent was evaporated in vacuum to dryness. Yield: 1.5 g (22%, R-PAI).

The aqueous phase was evaporated to dryness, resulting honey-like semi-solid product. Yield: 9.47 g (103.3%).

$^1$-NMR—0.65 equivalent of acid formed the salt.

Example 5.5

3.84 g of citric acid was dissolved in 50 ml water and 10.26 g of rasagiline base was added to the solution, which was stirred at room temperature for 3 hours.

The reaction mixture was extracted with 2×50 ml toluene. The combined toluenic extract was evaporated to dryness in vacuum. IPA was added to the residue and then evaporated to dryness. Yield: 3.92-4.13 g (R-PAI) (38.2-40.2%).

The aqueous phase was evaporated to dryness, resulting honey-like semi-solid product. Yield: 10.54-9.73 g.

$^1$H-NMR—0.58 equivalent of acid formed the salt.

Example 5.6

3.84 g of citric acid was dissolved in 50 ml water and 10.26 g of rasagiline base was added to the solution, which was stirred for 3 hours at 60° C.

The reaction mixture was extracted with 2×50 ml toluene. The combined toluenic extract was evaporated to dryness in vacuum. IPA was added to the residue and then evaporated to dryness. Yield: 3.92-4.13 g (R-PAI) (38.2-40.2%).

The aqueous phase was evaporated to dryness, resulting honey-like semi-solid product. Yield: 10.54-9.73 g.

$^1$H-NMR—0.58 equivalent of acid formed the salt.

Example 5.7

3.84 g of citric acid was dissolved in 50 ml water and 10.26 g of rasagiline base was added to the solution, which was stirred for 42 hours at 25° C.

The reaction mixture was extracted with 2×50 ml toluene. The combined toluenic extract was evaporated to dryness in vacuum. IPA was added to the residue and then evaporated to dryness. Yield: 3.92-4.13 g (R-PAI) (38.2-40.2%).

The aqueous phase was evaporated to dryness, resulting honey-like semi-solid product. Yield: 10.54-9.73 g.

$^1$H-NMR—0.58 equivalent of acid formed the salt.

Example 5.8

1.92 g of citric acid was dissolved in 25 ml water and 5.13 g of rasagiline base was added to the solution, which was stirred at room temperature for 16 hours. The reaction mixture was extracted with 2×30 ml toluene and the toluenic extract was evaporated to dryness. Yield: 2.19 g (R-PAI; 42.7%).

The aqueous phase was dried by lyophilization. The product was crystalline-like foam which then became honey-like semi-solid.

$^1$H-NMR—0.55 equivalent of acid formed the salt.

Example 5.9

1.92 g of citric acid was dissolved in 25 ml water and 5.13 g of rasagiline base was added to the solution, which was stirred at room temperature for 9 days. The solid was filtered off, washed with 5 ml water, and dried with air. Yield: 0.31 g (6%, R-PAI), Mp.: 39.3-41.0° C.

The aqueous phase was lyophilized. The crystalline-like foam was formed which became honey-like semi-solid in a few hours.

$^1$H-NMR—0.35 equivalent of acid formed the salt.

Example 5.10

1.6 g of citric acid was dissolved in 10 ml water and 1.0 g of rasagiline base was added to the solution, which was stirred at room temperature. The solvent was removed by lyophilization. The product was crystalline-like foam which became semi-solid after a few hours.

$^1$H-NMR—1.2 equivalent of acid formed the salt.

Example 5.11

1.92 g of citric acid was dissolved in 15 ml IPA and 1.71 g of rasagiline base was added to the solution, which was stirred at room temperature for 2 hrs. No R-PAI was detected by TLC. The solvent was removed in vacuum. Yield: 3.85 (106%)

The foam-like semi-solid product became honey-like upon contacting with the humidity in the air.

Example 5.12

1.92 g of citric acid was dissolved in 15 ml IPA and 3.42 g of rasagiline base was added to the solution, which was stirred at room temperature for 2 hours. The reaction mixture became clear, which was monitored by TLC (hexane: EtOAc=1:1). The traces of R-PAI was detected. The solvent was removed in vacuum. The residue was slurred in 2×30 ml toluene. The combined toluenic phase was evaporated to dryness. Yield: 0.65 g (19%; R-PAI).

The crude product was dissolved in IPA and the solution was evaporated to dryness, resulting honey-like product.

Example 5.13

1.92 g of citric acid was dissolved in 15 ml IPA and 5.13 g of rasagiline base was added to the solution, which was stirred at room temperature for 2 hours. The reaction was monitored by TLC. Free R-PAI was present. The solvent was removed in vacuum. The residue was slurred in 2×30 ml toluene. The combined toluenic phase was evaporated to dryness. Yield: 2.47 g (48%; R-PAI).

The crude product was dissolved in IPA and the solution was evaporated to dryness. A honey-like product was obtained.

Example 5.14

1.92 g of citric acid was dissolved in 15 ml methanol and 1.71 g of rasagiline base was added to the solution, which was stirred at room temperature for 22 hours and was then evaporated to dryness. Yield: 3.77 g (103.86%).
$^1$H-NMR—0.72 equivalent of acid formed the salt.

Example 5.15

1.92 g of citric acid was dissolved in 20 ml methanol and 3.42 g of rasagiline base was added to the solution, which was stirred at room temperature for 22 hours and was then evaporated to dryness. Yield: 5.48 g-103.6%. By TLC, the free R-PAI in product was detected.
$^1$H-NMR—0.5 equivalent of acid formed the salt.

Example 5.16

1.92 g of citric acid was dissolved in 25 ml methanol and 5.13 g of rasagiline base was added to the solution, which was stirred at room temperature for 22 hours and was then evaporated to dryness. Yield: 7.32 g-103.8%. By TLC, the free R-PAI in product was detected.
$^1$H-NMR—0.33 equivalent of acid formed the salt.

Example 5.17

1.92 g of citric acid was stirred in 20 ml EtOAc and 1.71 g of rasagiline base was added to the solution, which was stirred for additional 72 hours. The reaction was monitored by TLC. The free rasagiline base was detected.

The solution was decanted from the reaction mixture. The solvent was removed under vacuum. Yield: 1.32 g (77%) R-PAI.

The isolated R-PAI was re-dissolved in 20 ml ethylacetate and and 10 ml water was added to the mixture. The reaction mixture was stirred for 22 hours. The unreacted R-PAI remained in the EtOAc phase according to the data of TLC. The phases were separated. The organic phase was evaporated to dryness. Yield: 0.13 g (7.6%) R-PAI.

Example 5.18

1.92 g of citric acid was stirred in 20 ml EtOAc and 3.42 g of rasagiline base was added. The solution was stirred for additional 72 hours. The reaction was monitored by TLC. The free rasagiline base was detected.

The solution was decanted from the reaction mixture. The solvent was removed under vacuum. Yield: 2.87 g (83.9%, R-PAI).

The isolated R-PAI was re-dissolved in 20 ml ethylacetate and 10 ml water was added to the mixture. The reaction mixture was stirred for 22 hours. The unreacted R-PAI remained in the EtOAc phase according to the data of TLC. The phases were separated. The organic phase was evaporated to dryness. Yield: 0.62 g (18%-R-PAI).

Example 5.19

1.92 g of citric acid was stirred in 25 ml EtOAc and 5.13 g of rasagiline base was added. The reaction mixture was stirred for additional 72 hours. The reaction was monitored by TLC. The free rasagiline base was detected in all cases.

The solution was decanted from the reaction mixture. The solvent was removed in vacuum. Yield: 4.49 g (87.5%, R-PAI).

The isolated R-PAI was re-dissolved in 20 ml ethylacetate and and 10 ml water was added to the mixture. The reaction mixture was stirred for 22 hours. The unreacted R-PAI remained in the EtOAc phase according to the data of TLC. The phases were separated. The organic phase was evaporated to dryness. Yield: 1.76 g (34.3% R-PAI).

Example 5.20

1.92 g of citric acid was stirred in 25 ml toluene and 1.71 g rasagiline base was added to the mixture. The heterogenous mixture was stirred at room temperature for 24 hours. The solution was decanted from the reaction mixture. The toluenic phase was evaporated to dryness. Yield: 1.58 g (92.4%); (R-PAI by TLC).

The isolated R-PAI was re-dissolved in 10 ml of toluene and was returned to the solid phase. 20 ml water was added to the heterogenous mixture and stirred for 3 hours. The reaction was monitored by TLC. The phases were separated. The toluenic phase was evaporated to dryness. Yield: 0.12 g (7%), R-PAI was detected according to the data of TLC. The aqueous phase was evaporated to dryness.

Example 5.21

1.92 g of citric acid was dissolved in 20 ml acetone and 1.71 g of rasagiline base was added to the reaction mixture, which was stirred at room temperature for 2 hours. The reaction was monitored by TLC. No R-PAI was detected.

The solution was decanted from the honey-like precipitation. Yield: 2.43 g (66.9%).

The acetonic solution was evaporated to dryness. Honey-like product was obtained. Yield: 1.48 (40.7%).

The total yield was 107.6% (acetone remained in the product).

Example 5.22

1.92 g of citric acid was dissolved in 20 ml acetone and 3.42 g of rasagiline base was added to the mixture, which was stirred at room temperature for 22 hours. R-PAI was detected by TLC. The acetonic solution was decanted from the honey-like precipitation. Yield: 4.41 g (82.6%) semi-solid product.

The acetonic phase evaporated to dryness. Yields: 1.34 g (25.1%)

TABLE 5a

Summary of Experimental Results

| Example | Solvent | Proportions of reagents (mole) Citric acid, mole | Rasagiline base, mole | Extracted R-PAI (%) (*Filtered) | Equivalent of Citric acid in the salt by NMR | R-PAI By TLC | pH (after extraction of R-PAI) |
|---|---|---|---|---|---|---|---|
| 5.11 | IPA | 1 | 1 | | | − | |
| 5.1 | Water | 1 | 1 | Extr. with Toluene 0.06 g-1.75% | | − | |
| 5.4 | Water | 1 | 2 | 1.51 g (22%) | | + | |
| 5.5 | Water | 1 | 3 | 4.13 g (40.2%) | | + | |
| 5.6 | Water 60° C. | 1 | 3 | 4.44 g (43.3%) | | + | |
| 5.7 | Water 2 days | 1 | 3 | 3.92 g (38.2%) | | + | |
| 5.9 | Water | 1 | 3 | 0.31 g (6%) | 0.35 | + | |
| 5.3 | Water | 1 | 2 | | 0.48 | + | |
| 5.13 | IPA | 1 | 3 | 2.47 g (48%) | 1.55 | + | |
| 5.12 | IPA | 1 | 2 | 0.65 g (19%) | 1.62 | + | |
| 5.10 | Water | 1 | 0.7 | lyophilized | 1.2 | − | |
| 5.8 | Water | 1 | 3 | Extr. 2.19 g (42.7%) | | + | |
| 5.2 | Water | 1 | 1 | lyophilized | 0.73 | − | |
| 5.14 | MeOH | 1 | 1 | | 0.72 | − | 3.53 (3.49) |
| 5.15 | MEOH | 1 | 2 | | 0.5 | + | 4.88 (4.46) |
| 5.16 | MeOH | 1 | 3 | | 0.33 | + | 6.09 (4.66) |
| 5.20 | Toluene | 1 | 1 | | | + | |
| 5.17 | EtOAc | 1 | 1 | | 7.6 | + | (3.41) |
| 5.18 | EtOAc | 1 | 2 | | 18 | + | (4.43) |
| 5.19 | EtOAc | 1 | 3 | | 34.3 | + | (4.90) |
| 5.21 | Acetone | 1 | 1 | | | − | |
| 5.22 | Acetone | 1 | 2 | | | + | |

Discussion of Example 5

Rasagiline base readily forms salts with citric acid in almost all various types of solvents, but most readily in water and in alcohols.

Mono-rasagiline citrate salt forms and is stable in most solvents. A few percent of free rasagiline may be extracted from the aqueous solution of this salt.

Di- and tri-citrates are not as stable in the aqueous and other solutions (alcohol, MEK, acetone). Free rasagiline base may be detected by TLC and extracted with toluene.

The separation of free rasagiline base from the aqueous solution of di- and tri-rasagiline citrates resulted the change of pH of the solution, as shown in Table 5a.

All of the rasagiline citrate salts are hygroscopic salts and readily absorb the humidity from air. The rasagiline citrates more readily form strong solvates with the solvents in which the salt formation occurred (up to 10%).

The aqueous solution of rasagiline citrates may be dryed by lyophilization.

The NMR study of rasagiline citrate in the above examples provides information about the composition (proportion) of the samples and not the proportion of the free base and the charged base (cationic form) with citric acid.

Above examples also demonstrate that the ratio of rasagiline Base:Citric acid used correlates with content of the "extractable" rasagiline base and amount of unreacted Citric acid found in the salt by NMR. The results are summarized in the Table 5b below.

TABLE 5b

Effect of salt composition on content of extractable Rasagiline base

| Salt | Ratio Base to acid mole:mole | Equivalent of Citric acid by $^1$HNMR for salt prepared in: Methanol | Water | Content of extractable base (toluene) % on total base content |
|---|---|---|---|---|
| Mono-citrate | 0.7:1.0 | N.A. | N.A. | N.A. |
| Mono-citrate | 1.0:1.0 | 0.72 | 0.73 | 1.75-3.6 |
| Di-citrate | 2.0:1.0 | 0.50 | 0.48 | 22.0 |
| Tri-citrate | 3.0:1.0 | 0.33 | 0.35 | 42.7 |

The data in Table 5b show that excess of Citric acid dramatically reduce the content of extractable rasagiline base.

It is concluded that lower content of extractable Rasagiline base (or higher content of Citric acid) provides higher stability of Rasagiline in the salt. Therefore, the most stable rasagiline citrate salt is mono-citrate salt and the most stable compositions of rasagiline citrate are compositions containing less than 1 mole of Rasagiline base per 1 mole of Citric acid.

Example 6

Evaluation of Rasagiline Citrate Salts

Three samples of rasagiline citrates prepared in Examples 4b, 4c and 4d were exposed to atmospheric air in open dishes at ambient temperature. The changes were observed and recorded. The results are presented in the Table 6a below:

TABLE 6a

Changes in Citrate salts exposed to atmosphere at ambient temperature

| Time of exposure (hrs:min) | Example 4b Mono- | Example 4c Salt type Di- | Example 4d Tri- |
|---|---|---|---|
| 0:00 | Powder | Powder | Powder |
| 0:30 | | Powder | Powder |
| 0:50-1:00 | Sticky aggregates | Powder | Sticky aggregates |
| 1:50-2:00 | Semi-solid | Powder | Sticky aggregates |
| 5:00 | Honey-like semi-solid | Lump powder | Semi-solid |
| 6:00 | Syrup | Sticky aggregates | Semi-solid |
| 7:00 | Syrup | Sticky aggregates | Honey-like semi-solid |
| 25:00 | N.A. | Sticky aggregates + semi-solid | N.A. |

Discussion

The results in Table 6a show that all three salts disclosed above are highly hygroscopic when exposed to atmosphere at ambient temperature. The results also show that there is no significant difference in hygroscopicity between the mono-, di- and tri-rasagiline citrates. All three salts appear as hydrates.

Parkinsonian patients suffer from swallowing disorders which prevent them from swallowing standard tablets or capsules. (Potulska A., "Swallowing disorders in Parkinson's disease", *Parkinsonism Relat. Disord.* (2003 August) Vol. 9 (6), pages 349-53). This difficulty hinders their treatment by reducing patient compliance. Patients will be more likely to comply to dosage regimens if swallowing tablets or capsules is not required.

A means to avoid the absorption of rasagiline in the stomach, and to eliminate the need for swallowing tablets, is by absorption of rasagiline into the body before reaching the stomach. Such absorption of rasagiline, and hence resolution of both problems, can be accomplished by contact with the buccal, sublingual, pharyngeal and/or esophageal mucous membranes. To accomplish this, oral compositions can be designed to rapidly disperse within the mouth to allow maximum contact of rasagiline with the buccal, sublingual, pharyngeal and/or esophageal mucous membranes. The unexpectedly high hygroscopicity of the citrate salts of rasagiline is particularly suitable for such oral formulations.

Another three samples of rasagiline citrates prepared in Examples 4b, 4c and 4d were stored in closed transparent glass vials sealed with paraffin film in refrigerator at 7±2° C. The changes were observed and recorded. The results are presented in the Table 6b below:

TABLE 6b

Appearance of Citrate salts stored in refrigerator

| Time of Storage, month(s) | Example 4b Monobasic | Example 4c Salt type Dibasic Appearance: | Example 4d Tribasic |
|---|---|---|---|
| 0 | White powder | White powder | White powder |
| 3 | White powder | White powder | White powder |
| 6 | White powder | White powder | White powder |

Discussion

The results in Table 6b show that all three salts could be stored for a long time (more than 6 month) under sealed condition at low temperature (~7° C.) with no change of color and appearance in spite of their high hygroscopicity at ambient temperature. This finding was surprising and may be the result of effect of temperature on hygroscopic point of Rasagiline citrates.

The results in Table 6b also show that all three salts could be handled and processed under controlled conditions such as low temperature and low humidity without change of their physical appearances, despite their high hygroscopicity.

Example 7

Characterization of Rasagiline Citrate—XRD Analysis

Samples were tested using Scintag X-Ray powder diffractometer model X'TRA, Cu-tube, solid-state detector.

Scanning Parameters

Range: 2-40 degrees two-theta.

Scan mode: Continuous scan

Step size: 0.05 deg.

Rate: 3 deg./min.

Sample holder: a round standard aluminum sample holder with round zero background quartz plate with cavity of 25 (diameter)*0.5 (dept.) mm.

TABLE 7

Characteristic XRD peak positions of the different samples (±0.2 degrees two-theta)

| | Form | | | |
|---|---|---|---|---|
| Sample | Amorphous form 1 | Amorphous form 2 | Amorphous form 3 | Amorphous form 4 |
| Peak positions | Not applicable | Not applicable | Not applicable | Not applicable |

Discussions

Results in Table 7 show that samples of rasagiline citrate do not show any characteristic peaks in XRD analysis, which indicates that rasagiline citrate samples prepared are amorphous.

Example 8

Comparison of Properties of Rasagiline Citrate to Other Salts

Rasagiline citrate exhibits properties which are different from the properties of other citrate salts as shown in Table 8a, and also different from the properties of other rasagiline salts as shown in Table 8c.

TABLE 8a

Summary of Citrate of various drug substances

| Citrate Salt of Drug Substance | Polymorph | References |
|---|---|---|
| 5,8,14-Triazatetracyclo-hexdecqa-2(11),3,5,7,9-pentaene | Crystalline | WO 02/092597 |
| 2-hydroxy-3-[5-(morpholin-4-ylmethol)pyridine-2-yl]1H-indole-5-carbonitrile | Crystalline | WO 07/089191 |
| 2-(6-{2-[(2(2R)-2-Methyl-1-pyrrolidin-1-yl]-ethyl}-2-naphthalen-2-yl)-2H-pyridazin-3-one | Crystalline | US 2005/0256127 |
| 4-(3,4-dichlorophenyl)-2-[2-94-Methlpiperazin-1-yl)-Bennylidene]-thiomorpholin-3-one | Crystalline | US 2003/0181444 |
| 4-[(4-Methyl-1-piperazinyl)methyl]-N-[4-methyl-3-[[(4-(3-pyridinyl)-2-pyrimidinyl]amino]phenyl]-benzamide | Crystalline | US 2008/0249104 |
| 5-(5-Fluoro-2-oxo-1,2-dihydro-indol-3-ylidenemethyl)-2,4-dimethyl-1H-pyrrole-3-carboxylic acid (2-pyrrolidin-1-yl-ethyl)-amide | Crystalline | US 2008/0275101 |
| 3-{(3R,4R)-4-methyl-3-[methyl-(7H-pyrrole]2,3-d]pyrimidin-4-yl)-amino]-piperidin-1-yl}-3-oxo-propionitrile | Crystalline | US 2005/0159434 |
| Decitabine | Crystalline | US 2006/0069060 |

As shown in Table 8a, unlike citrate salts of other drug substance, the rasagiline citrate salts are amorphous. No crystalline forms of rasagiline citrate have been detected.

TABLE 8b

Summary of Properties of Rasagiline Base and Citric Acid

| | Hygroscopicity by KF | Water solubility (mg/ml) | References |
|---|---|---|---|
| Solid R-PAI (Free Base) | Not hygroscopic | low | US 2008/0161408 |
| Citric Acid | low | 1330 | "Pharmaceutical Excipients" database |

TABLE 8c

Summary of Properties of Rasagiline Salts

| R-PAI base/ R-PAI salts | Hygroscopicity by KF | Water solubility (mg/ml) | References |
|---|---|---|---|
| Chloride | Not hygroscopic | 238 | U.S. Pat. No. 5,457,133 |
| Mesylate | Not hygroscopic | 635 | U.S. Pat. No. 5,532,415 |
| Tartrate | Not hygroscopic | 33 | U.S. Pat. No. 5,532,415 |
| Maleate | N.A. | >=1000 | U.S. Pat. No. 5,532,415 |
| Sulphate | N.A. | 485 | U.S. Pat. No. 5,532,415 |
| Tosylate | N.A. | 60-70 | U.S. Pat. No. 5,532,415 |
| Fumarate | N.A. | 95 | U.S. Pat. No. 5,532,415 |
| Phosphate | N.A. | >=720 | U.S. Pat. No. 5,532,415 |
| Esylate | N.A. | >=300 | U.S. Pat. No. 5,532,415 |
| Acetate | N.A. | >=720 | U.S. Pat. No. 5,532,415 |
| Tannate | <10% (R-PAI content related) | low | U.S. Pat. No. 7,547,806 |
| Citrate | Highly hygroscopic | Extremely High (Higher than rasagiline maleate) | |
| Edisilate | Not hygroscopic | 342.5 | WO 2008/019871 |
| Oxalate | Not hygroscopic | 19.7 | WO 2008/019871 |

The results in Table 8b and 8c show that compared to rasagiline base and other rasagiline salts, rasagiline citrate salt exhibits the highest water solubility and highest hygroscopicity.

What is claimed is:

1. Mono-rasagiline citrate.
2. The mono-rasagiline citrate of claim 1, wherein the rasagiline content is between 42% and 52% by weight based on the total weight of the mono-rasagiline citrate.
3. The mono-rasagiline citrate of claim 1, wherein the water content in the mono-rasagiline citrate, as determined by Karl Fischer analysis is less than 5%.
4. A composition comprising the mono-rasagiline citrate of claim 1 and a carrier.
5. The composition of claim 4, further comprising rasagiline base.
6. The composition of claim 5, wherein the rasagiline base is present in an amount of less than 5% based on the total rasagiline content of the composition.
7. The composition of claim 4, which is free of rasagiline base.
8. The composition of claim 4, wherein the rasagiline content present in the form of mono-rasagiline citrate is more than 50% of the total rasagiline content in the composition.
9. The composition of claim 4, wherein the mono-rasagiline citrate is mixed with a polymer.
10. The composition of claim 4, wherein the composition is a pharmaceutical composition and the carrier is a pharmaceutically acceptable carrier.
11. The composition of claim 10, further comprising stearic acid.
12. The composition of claim 10 in the form of a tablet or a transdermal patch.

13. A process for manufacture of the mono-rasagiline citrate of claim 1, comprising:
- a) combining a solution of citric acid with rasagiline base to form a first mixture;
- b) adding a solvent to the first mixture to form a second mixture;
- c) completely removing liquid from the second mixture; and
- d) recovering the mono-rasagiline citrate.

14. The process of claim 13, wherein the solvent added in step b) is acetone, and wherein in step c) the liquid is removed at ambient temperature and at reduced pressure.

15. A process for manufacture of the composition of claim 4, comprising:
- a) obtaining mono-rasagiline citrate; and
- b) admixing the mono-rasagiline citrate with the carrier.

16. A method of treating a human subject afflicted with Parkinson's disease comprising administering to the human subject an amount of the composition of claim 10, effective to treat the human subject.

\* \* \* \* \*